United States Patent [19]

Bazika et al.

[11] 4,057,999
[45] Nov. 15, 1977

[54] APPARATUS FOR TESTING ENGINE OIL

[75] Inventors: Vladimír Bazika; Přemysl Pražak; Dana Havelková, all of Prague, Czechoslovakia

[73] Assignee: CKD Praha, Oborovy podnik, Prague, Czechoslovakia

[21] Appl. No.: 705,000

[22] Filed: July 14, 1976

[30] Foreign Application Priority Data

July 30, 1975 Czechoslovakia ............... 5340/75

[51] Int. Cl.² ...................... G01N 11/00; G01N 33/26
[52] U.S. Cl. ......................................... 73/53; 73/61.2
[58] Field of Search .................. 73/53, 61.2, 15 R, 64

[56] References Cited

U.S. PATENT DOCUMENTS 3,059,467  10/1962  Meguerian et al. ............... 73/61.2
3,108,468  10/1963  Mickel ........................... 73/61.2

FOREIGN PATENT DOCUMENTS 129,872  11/1960  U.S.S.R. ........................ 73/61.2

Primary Examiner—Jerry W. Myracle
Assistant Examiner—Joseph W. Roskos

[57] ABSTRACT

An apparatus for testing engine oils and in particular oils to be used in compression ignition engines. The apparatus includes a receptacle in which a sample of the liquid oil to be tested is poured. The receptacle has a cover plate with an opening. A test plate is mounted in the opening of the cover plate and seals the receptacle. A shaft with radial projections is mounted in the receptacle and submerged in the liquid oil to be tested. When the shaft rotates the projections splash oil against the test plate. First temperature sensing means are mounted in the test plate and second temperature sensing means are submerged in the liquid oil. A heating element is mounted over the cover plate. The first temperature sensing means are operatively connected to the heating element via a thermal regulator to thereby maintain the test plate at a preselected temperature. The second temperature sensing means serve to maintain the liquid oil sample at a preselected temperature.

1 Claim, 1 Drawing Figure

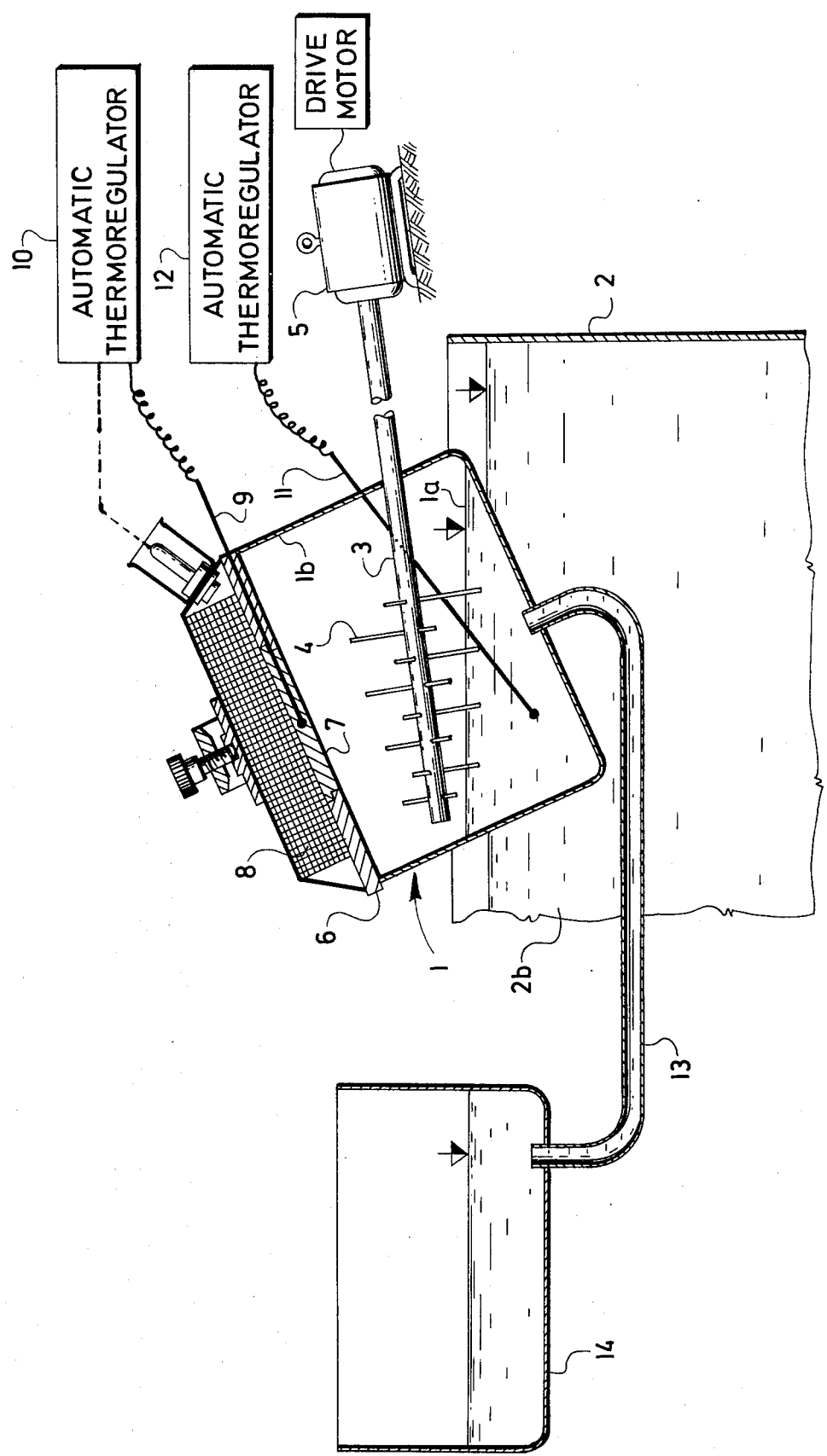

APPARATUS FOR TESTING ENGINE OIL

BACKGROUND OF THE INVENTION

The present invention relates to an apparatus for testing motor oil. The apparatus has automatic temperature control means for a test plate and the oil to be tested. The oil level during operation is automatically compensated.

As is well-known, one of the most important characteristics for lubricating oils for internal combustion engines, and more particularly for compression ignition engines, is their heat-resistance. The higher the heat-resistance, the better is the capability of the lubricating oil to keep the pistons of the engine clean. Deposits and films generally form in the region of the first piston ring even when the engine is hot. The operating temperatures may sometimes reach values exceeding 230° C.

The quality of suitability of an engine oil has to be checked by subjecting it to long-running tests effected directly in the engine. Such tests may take a hundred or even more hours each. After the test, the oil condition and piston appearance have to be checked.

Since such tests are expensive and time-consuming intensive, efforts are continuously made to find a less expensive and shorter laboratory test.

The apparatus of the state of the art for carrying out such tests generally include complex and costly installations which are based on the principle of spraying oil onto a test plate which is secured on the cover of a vessel containing oil, the test plate being heated by an electrical heating element.

The aforementioned test equipment has several drawbacks. The operating reliability of such equipment is relatively low; their selectivity is poor as well. Furthermore, the maintenance of such equipment is costly because the temperature of both the test plate and the oil to be tested as well as the compensation for oil losses caused by evaporation of its light-weight fractions must be closely supervised by an attendant. Apart from this, the equipment of the state of the art has certain limitations; for example, the temperature of the oil to be tested cannot exceed a value of 330° C at the most and the duration of the complete test is also a factor to be considered. It has furthermore been ascertained that a rectangular shape of the test plate is disadvantageous since it is difficult to precisely manufacture such plates to perfectly fit the plate on the cover in order to seal it. Oil leakage into the space between the plate and the cover negatively influences the test results.

SUMMARY OF THE INVENTION

It is an object of this invention to provide an apparatus for testing engine oil in which the disadvantages of the aforedescribed devices of the prior art are eliminated or at least mitigated. The improved apparatus of this invention is adapted for testing engine oil, especially compression ignition engine oil. The device of this invention includes a receptacle to be filled with the oil to be tested, a rotary sprayer provided with spikes which are designed to submerge, during operation of the device, in the oil contained in the receptacle. This receptacle is partly submerged in a cooling tank and is sealed on the top by a cover in which a test plate is inserted. The test plate is adapted to be heated by an electrical heating element. The improvement of the apparatus resides in that within the center of the circular test plate a first temperature sensing means of a first thermoregulator is provided while a second temperature sensing means of a second thermoregulator is submerged into the oil to be tested. The oil receptacle is in communication with an oil level compensating tank.

As described hereinabove, the essential advantage of the present invention resides in that the temperature of both the test plate and the oil to be tested is maintained by means of automatic thermoregulating means at predetermined values and that the oil in the receptacle is automatically kept at a constant level. The test plate can be more easily and advantageously manufactured and can be better fitted and sealed in the receptacle cover with the present invention. The automatic regulation of the temperature of both the test plate and the oil to be tested together with the circular shape of the test plate make it possible for the results to be evaluated with a high selectivity or distinguishing capability. The testing apparatus in accordance with this invention makes it possible to determine oil quality differences at only a 10° C test plate temperature change. Due to the automatic oil level compensation, only 0.5 liter of oil is required for a single test. The automation of the testing process reduces the time of attendance necessary by the personnel operating the device. Thus, only an occasional inspection is required and subjective influences upon the test results are eliminated.

BRIEF DESCRIPTION OF THE DRAWING

In order that the invention may be better understood and carried into practice, a preferred embodiment thereof will hereinafter be described with reference to the accompanying single FIGURE of the drawing which illustrates schematically the apparatus of the invention. However, the drawing is not intended to limit in any way the scope of the invention.

DETAILED DESCRIPTION

As is evident from the drawing, a receptacle 1, containing oil to be tested, is partly submerged in a cooling medium 2b stored in a cooling tank 2. A shaft 3 of a rotary sprayer extends through an opening 1a of a side wall 1b of the oil receptacle 1. The shaft 3 has a plurality of spikes 4 affixed thereto which extend generally radially therefrom and serve for spraying oil onto a test plate 7. The shaft 3 is driven rotatably by an electric motor 5 as indicated by the arrow in the drawing. The oil receptacle is closed on its top side by a removable cover 6. A test plate 7 is mounted with a tight fit in the central portion of the cover 6. The test plate 7 is made from a light alloy suitable for piston manufacture. The test plate 7 has a circular shape which makes possible, apart from an easier and more precise manufacture, to perfectly fit and seal the plate in the cover. The manufacture of the apparatus of this invention permits an easier choice of tolerances for the outer plate dimensions to meet various test temperature ranges. An electrical heating element 8 is mounted adjacent to the cover 6. A conventional temperature sensor 9 extends through the cover 6 into the test plate 7 and is connected to an automatic thermoregulator 10. Another temperature sensor 11 extends through the opening 1a into the oil receptacle 1 and is submerged in the oil to be tested. The temperature sensor 11 is connected to another thermoregulator 12. The oil receptacle 1 fluidly communicates via pipe 13 with a compensating tank 14 so that changes in oil level in receptacle 1 are compensated for in the receptacle 1.

The device of the invention operates as follows:

The oil to be tested is poured into the receptacle 1 which is then closed by the cover 6 together with the test plate 7. The electrical heating element 8 is then mounted in the cover 6. The heating element 8 heats the test plate 7, disposed within the center of the cover 6, to a preselected temperature. A constant temperature of the test plate 7 is maintained by the first automatic thermoregulator 10, via feed-back control connection to the heating element 8, by means of the first temperature sensor 9 inserted in the test plate 7. After the desired temperature of the test plate 7 has been attained, the electric motor 5 is switched on to rotatably drive the shaft 3 of the sprayer, the spikes 4 of which, when emerging from below the oil level, spray the oil against the test plate 7. By contacting the hot test plate 7, the oil to be tested is intensely heated during the test so that the oil receptacle 1 has to be cooled by a cooling medium 2b in the cooling tank 2. A constant predetermined temperature of the oil to be tested, such as, for example, 80° C, is maintained by the second automatic thermoregulator 12 via the second temperature sensor 11 placed in the receptacle 1. The engine oil test result is evaluated according to the amount, color, and superficial distribution of deposits on the test plate.

The test apparatus according to the invention can be used for testing all types of engine oils to be exposed to relatively high ranges of temperatures of from 250° to 400° C, depending upon the quality of the oil to be tested.

Although the invention has been illustrated and described with reference to a single preferred embodiment thereof, it is to be expressly understood that it is in no way limited by the disclosure of such a preferred embodiment, but is capable of numerous modifications within the scope of the appended claims.

What is claimed is:

1. An apparatus for testing engine oils, and in particular, oils to be used in compression ignition engines, comprising in combination, a receptacle adapted to receive a liquid oil sample to be tested;

a cover plate having an opening and mounted on said receptacle;

a shaft having a plurality of projections extending therefrom, rotatably mounted in said receptacle, said projections being adapted to submerge into and emerge from said liquid oil and to splash said oil against said cover plate;

driving means operatively connected to said shaft for rotating it;

a test plate mounted in said opening of said cover plate to thereby seal said receptacle;

first temperature sensing means operatively mounted in said test plate;

heating means adapted to heat said test plate;

first thermal regulating means operatively connected to said heating means, on the one hand, and said first temperature sensing means, on the other hand, and adapted to maintain said test plate at a predetermined temperature;

second temperature sensing means operatively mounted in said receptacle to sense the temperature of said oil therein and to maintain it at a predetermined temperature; and second thermal regulating means operatively connected to said second temperature sensing means, whereby the oil deposited on the test plate by being splashed thereagainst by said rotating projections can be tested by visually evaluating it.

* * * * *